United States Patent [19]

Murata et al.

[11] Patent Number: 5,241,064
[45] Date of Patent: Aug. 31, 1993

[54] ENZYMATIC PROCESS FOR PREPARING OPTICALLY ACTIVE 3-SUBSTITUTED AZETIDINONES

[75] Inventors: Masayoshi Murata; Toshiyuki Chiba; Fumiyuki Shirai, all of Osaka; Kenichi Washizuka, Higashiosaka; Motohiro Hino, Tsuchiura, all of Japan

[73] Assignee: Fujisawa Pharmaceutical Co., Ltd., Osaka, Japan

[21] Appl. No.: 587,037

[22] Filed: Sep. 24, 1990

[30] Foreign Application Priority Data

Oct. 2, 1989 [GB] United Kingdom ............... 8922138
Feb. 13, 1990 [GB] United Kingdom ............... 9003264

[51] Int. Cl.$^5$ .................... C07D 205/08; C12P 41/00; C07F 7/18
[52] U.S. Cl. .................................. 540/362; 435/280; 556/418; 556/419
[58] Field of Search ................ 540/362; 435/280

[56] References Cited

U.S. PATENT DOCUMENTS 3,104,201  9/1963  Testa .................... 540/362
4,287,123  9/1991  Liu ....................... 540/200
5,017,484  5/1991  Nakamura ............. 435/280

FOREIGN PATENT DOCUMENTS 1815845  7/1970  Fed. Rep. of Germany .

OTHER PUBLICATIONS

Hatanaka, Tennen Yuki Kagobatsu Toronkai Koen Yoshishu, 1986, 28th 542-9 (and Abstract).
Hirai, Tet. Letters 30, 2555 (1989).
Ohta, Agric. Biol. Chem 44, 863 (1980).
Oritani, Agric. Biol. Chem 44, 2637 (180).
Perlmutter, Tet. Letters 29, 949-52 (1988).
Kametani, J. Amer. Chem Soc 102, 2060 (1980).
Iimori, Tet. Letters 27, 2149 (1986).
Melillo, Tet. Letters 21, 2783.
Monkiewicz, Acta Biotech. 5, 263 (1985).
Holley, J.A.C.S. 71, 2124 (1949).
Morrison "Organic Chemistry", 3rd Ed., 283–308 (1970).
Fersht, "Enzyme structure and Mechanism" (2nd ed) pp. 98–106 347–354 (1970).
Watson, "Molecular Biology of the Gene", vol. 1, pp. 387–392 (1970).
Streitweisen, "Introduction to Organic Chemistry" 2nd Ed pp. 575–586.

*Primary Examiner*—Mark L. Berch
*Attorney, Agent, or Firm*—Oblon, Spivak, McClelland, Maier & Neustadt

[57] ABSTRACT

Preparation of optically active 3-substituted azetidinones of the formula (I)

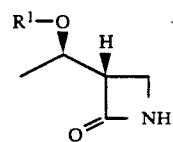

in which $R^1$ is a hydroxy-protective group wherein an allylic alcohol of the formula (II)

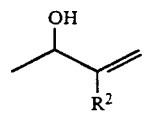

is acylated, then subjected to asymmetric enzymatic hydrolysis yielding the R-allylic alcohol. The hydroxyl group is protected and then stereoselectively reacted with an amine which is subsequently cyclized to yield the desired 3-substituted azetidinone. Two new species of microorganisms have been isolated, *Pimelobacter* sp. No. 1254 and *Bacillus megaterium* No. 1253 which exhibit stereoselective esterase activity.

4 Claims, No Drawings

ENZYMATIC PROCESS FOR PREPARING OPTICALLY ACTIVE 3-SUBSTITUTED AZETIDINONES

The present invention relates to a new process for preparing optically active 3-substituted azetidinones.

More particularly, the present invention relates to a new process for preparing optically active 3-substituted azetidinones, which are useful as an intermediate for manufacturing antimicrobially active $\beta$-lactam compounds.

In the field of $\beta$-lactam chemistry, it is well known that the compound of the following chemical formula is the principal intermediate for manufacturing $\beta$-lactam antibiotics such as penems, carbapenems, cephalosporins, and the like, and various methods therefor were investigated and reported until now. However, these methods were not so satisfactory in view of industrial manufacturing.

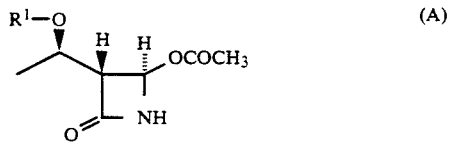
(A)

in which $R^1$ is hydroxy-protective group, particularly t-butyldimethylsilyl.

The inventors of the present invention have made an extensive study and succeeded in establishing the more stereospecific and more industrially valuable method for optically active 3-substituted azetidinones useful for production of the above principal intermediate (A).

Accordingly, the present invention provides a new process for preparing optically active 3-substituted azetidinones useful for industrial production of the above-identified principal intermediate (A).

Further, the present invention provides optically active new 1,3-disubstituted azetidinones, which are particularly useful for production of the principal intermediate (A) as mentioned above.

The optically active 3-substituted azetidinones prepared according to the new process of the present invention are known and can be represented by the following chemical formula, from which the principal intermediate (A) can be produced by known methods.

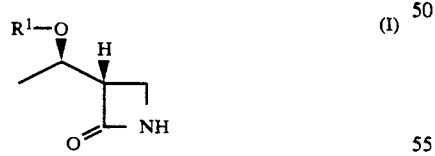
(I)

in which $R^1$ is as defined above.

Further, the optically active new 1,3-disubstituted azetidinones of the present invention can be represented by the following chemical formula.

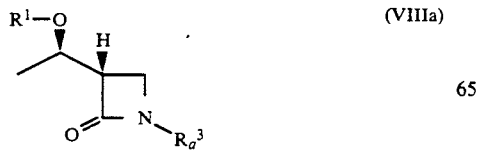
(VIIIa)

in which
$R^1$ is as defined above, and
$R_a^3$ is mono or diarylmethyl, in which the aryl moiety is substituted with at least one lower alkoxy group.

The new process of the present invention can be illustrated by the following reaction schemes.

Scheme I

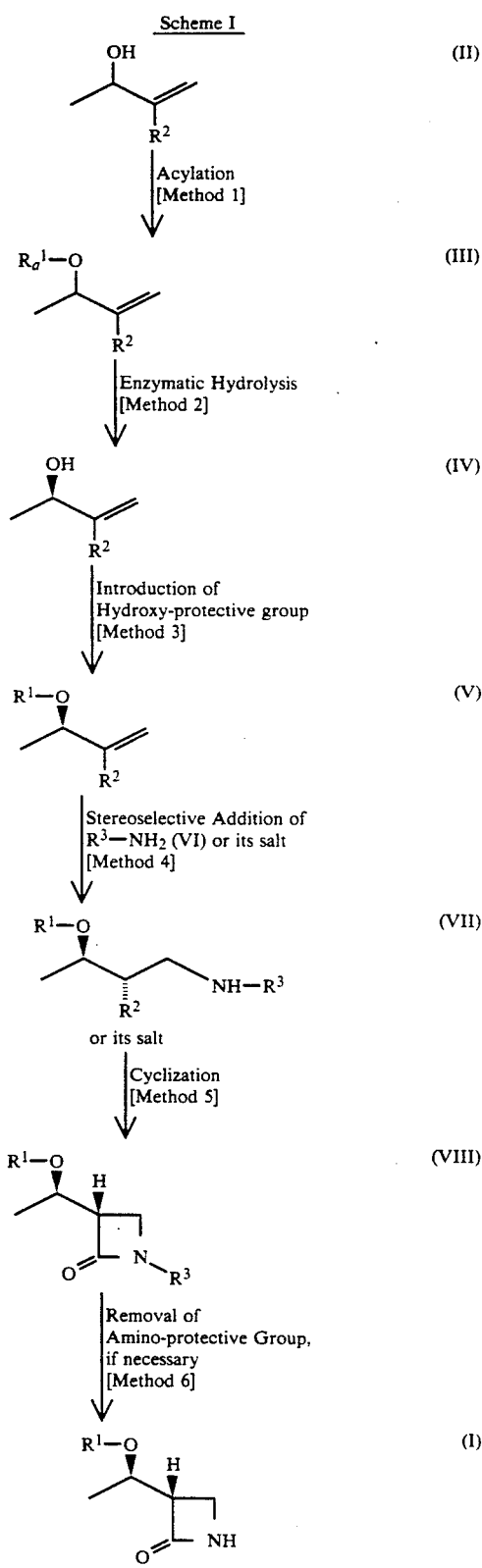

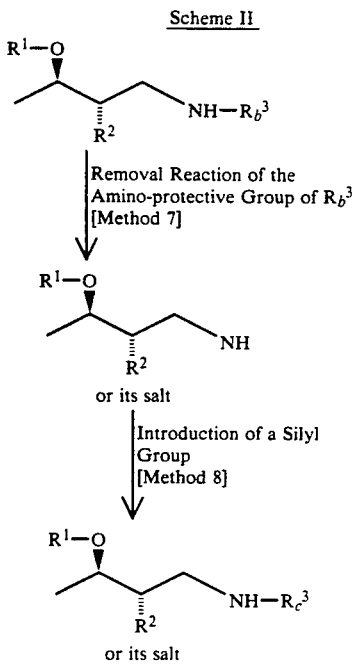

Scheme II in which
R[1] is as defined above,
$R_a^1$ is acyl,
R[2] is protected carboxy,
R[3] is hydrogen or amino-protective group,
$R_b^3$ is amino-protective group, and
$R_c^3$ is a silyl group.

In the description of the present specification, suitable illustration and examples of the various definitions to be included within the scope thereof are explained in detail as follows.

The term "lower" is intended to mean 1 to 6 carbon atom(s), preferably 1 to 4 carbon atom(s), unless otherwise indicated.

Suitable "hydroxy-protective group" for R[1] may include a conventional one used in the β-lactam field, for instance, trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; acyl derived, for example, from an organic carboxylic carbonic, or sulfonic acid such as phenyl-(or nitrophenyl-)(lower)alkoxycarbonyl (e.g. benzyloxycarbonyl, 4-nitrobenzyloxycarbonyl, etc.); and the like, in which more preferable one may be tri(lower)alkylsilyl, and the most preferable one may be 1-t-butyldimethylsilyl.

Suitable "acyl" for $R_a^1$ may include conventional one derived from an organic acid, which is removable by enzymatic hydrolysis, such as lower alkanoyl (e.g. formyl, acetyl, propionyl, butyryl, isobutyryl, valeryl, hexanoyl, etc.), and the like, in which the most preferable one may be acetyl.

"Protected carboxy" for R[2] may include esterified carboxy and suitable "ester" moiety in the esterified carboxy may include lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent, for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester); mono(or di or tri)halo(lower)alkyl ester (e.g. 2-iodoethyl ester, 2,2,2-trichloroethyl ester, etc.); lower alkenyl ester (e.g. vinyl ester, allyl ester, etc.); ar(lower)alkyl ester which may have at least one suitable substituent (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); and the like, in which more preferable one may be lower alkyl ester, and the most preferable one may be methyl ester and ethyl ester.

Suitable "amino-protective group" for R[3] may include one which is removable by hydrolysis, reduction, so-called oxidative debenzylation, and the like, and particularly, preferable examples of the amino-protective group removable by oxidative debenzylation may be mono(or di)arylmethyl, in which the aryl moiety is substituted with at least one lower alkoxy group (e.g. 2-methoxybenzyl, 4-methoxybenzyl, 4-ethoxybenzyl, 4-propoxybenzyl, 2,4-dimethoxybenzyl, 4,4'-dimethoxybenzhydryl, etc.); trisubstituted silyl such a tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.); lower alkenyl (e.g. allyl, etc.); and the like.

Suitable "mono(or di)arylmethyl, in which the aryl moiety is substituted with at least one lower alkoxy group" for $R_a^3$ may be the same as those exemplified for "amino-protective group" mentioned above.

Suitable "a silyl group" for $R_c^3$ may be "trisubstituted silyl" as mentioned in the explanation of "amino-protective group", which can be eliminated during cyclization reaction of Method 5, in which preferable example may be tri(lower)alkylsilyl, and the most preferable one may be trimethylsilyl.

The processes for the preparation of the object compound (I) of the present invention are explained in detail in the following.

(1) METHOD 1

The compound (III) can be prepared by acylating the compound (II).

The acylating agent to be used in this method is a conventional one which is capable of transforming a hydroxy group to an acyloxy group, for example, an organic acid such as an organic carboxylic acid, and the like, or a reactive derivative thereof.

Suitable reactive derivative of the organic acid may include, for example, an acid halide, an acid anhydride, an activated amide, an activated ester, and the like, and preferably an acid chloride and acid bromide; a mixed acid anhydride with an acid such as alkyl carbonate (e.g. methyl carbonate, ethyl carbonate, propyl carbonate, etc.); a symmetrical acid anhydride; an activated acid amide with a heterocyclic compound containing imino function such as imidazole, 4-substituted imidazole, dimethylpyrazole, triazole or tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N- hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, imidazole, and the like.

In case that the acylating agent is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethylene-ketene-N-cyclohexylimine, diphenylketene-N-cyclohexylimine, etc.); a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkyl-formamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, dichloromethane, dichloroethane, tetrahydrofuran, ethyl acetate, N,N-dimethylformamide, pyridine, hexamethylphosphoramide, etc., or a mixture thereof.

Among these solvent, hydrophilic solvents may be used in a mixture with water.

The reaction temperature is not critical and the reaction is usually carried out under cooling to warming.

(2) METHOD 2

The compound (IV) can be prepared by subjecting the compound (III) to enzymatic hydrolysis.

This hydrolysis is carried out in the presence of enzyme which is capable of transforming an acyloxy group to a hydroxy group such as esterase (e.g. lipase, etc.). The esterase is frequently found to exist widely, for example, in various kind of microorganisms which can be easily isolated from a soil sample and other sources by conventional means, and further can be easily selected from the collected cultures available in public facilities for culture collection such as ATCC (American Type Culture Collection, Maryland, USA), IAM (Institute of Applied Microbiology, University of Tokyo, Japan), IFO (Institute For Fermentation, Osaka, Japan), IID (The Institute for Infectious Diseases, University of Tokyo, Tokyo, Japan), CBS (Centraalbureau voor Schimmelcultures, Bearn, Netherlands), FERM [Fermentation Research Institute, Agency of Industrial Science and Technology, Chiba, Japan) and NRRL (Northern Utilization Research and Development Division, U.S. Department of Agriculture, Illinois, U.S.A.) and the like.

As to the microorganism having an esterase activity, there may be exemplified one belonging to the genus, Bacillus, Corynebacterium, Micrococcus, Flavovacterium, Salmonella, Staphylococcus, Vibrio, Microbacterium, Escherichia, Arthrobacter, Azotobacter, Alcaligenes, Rhizobium, Brevibacterium, Kluyvera, Proteus, Sarcina, Pseudomonas, Xanthomonas, Protaminobacter, Comamonus and the like.

Examples of the above microorganisms may be *Bacillus subtilis* IAM-1069, IAM-1107, IAM-1214, *Bacillus sphaericus* IAM-1286, *Corynebacterium equi* IAM-1308, *Micrococcus varians* IAM-1314, *Flavobacterium rigeus* IAM-1238, *Salmonella typhimurium* IAM-1406, *staphylococcus epidermidis* IAM-12906, *Microbacterium flavum* IAM-1642, *Alcaligenes faecalis* ATCC-8750, *Arthrobacter simplex* ATCC-6946, *Azotobacter vinelandii* IAM-1078, *Escherichia coli* IAM-1101, *Rhizobium japonicum* IAM-0001, *Vibrio metchnikovii* IAM-1039, *Brevibacterium helvolum* IAM-1637, *Protaminobacter alboflavum* IAM-1040, *Comamonas terrigena* IFO-12685, *Sarcina lutea* IAM-1099, *Pseudomonus schuylkilliensis* IAM-1055, *Xanthomonas trifolii* ATCC-12287 or the like.

In the enzymatic hydrolysis, the esterase can be preferably used in a form of a cultured broth obtained by culturing microorganisms having an esterase activity in a suitable manner, or of its processes material.

The processes material may include a supernatant solution or a filtrate obtained from the cultured broth in a conventional manner, or an isolated esterase or an esterase solution obtained by purification or partial purification of said supernatant or filtrate in a conventional manner.

The enzymatic hydrolysis is conducted by contacting the compound (III) with the cultured broth of the microorganism or its processed material in an aqueous medium such as water or a buffer solution (e.g. phosphate buffer, etc.) in a conventional manner.

Preferred pH of the reaction mixture, concentration of substrates, reaction time and reaction temperature may vary with characteristics of the cultured broth or its processed material to be used, or the compound (III) to be used. However, the reaction conditions are preferably selected from a range of at pH 4 to 10, more preferably at pH 6 to 8, at 20° to 50° C., more preferably at 25° to 35° C. for 5 to 100 hours.

Among the microorganisms mentioned above, Pimelobacter sp. No. 1254 and *Bacillus megaterium* No. 1253 have been newly isolated from soil samples collected from shizuoka-ken, Japan.

A lyophilized sample of the newly isolated Pimelobacter sp. No. 1254 has been deposited with the Fermentation Research Institute, Agency of Industrial Science and Technology (1–3, Higashi 1-chome, Tsukuba-shi, Ibaraki-ken, 305 Japan) under Budapest Treaty route with the deposit number of FERM BP-3087 on Sep. 4, 1990.

A lyophilized sample of the newly isolated *Bacillus megaterium* No. 1253 has been deposited with the same depository under Budapest Treaty route with the deposit number of FERM BP-3086 on Sep. 4, 1990.

It is to be understood that the microorganisms used in this method is not limited to the particular microorganisms described herein, which are given for the illustrative purpose only. This method also includes the use of any mutants, which are capable of converting the compound (III) to the compound (IV), including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

Taxonomic studies on Pimelobacter sp. No. $12^{54}$ are as follows.

The methods described in Bergey's Manual of Systematic Bacteriology (Volume 2) were employed principally for this taxonomic study.

(i) Morphological characteristics:

Morphological observation of strain No. 1254 was carried out with an optical microscope with cells cultured on nutrient broth (Difco) and trypticase soy agar (BBL) at 37° C. for 2 days.

Strain No. 1254, an irregular, nonsporing gram-positive rod, grew without motility in the presence of air. The cells were short rods. However the cells were morphologically changed to spheres under the stational phase.

These results are shown in Table 1.

(ii) Phylogenetical characteristics:

The cell wall peptidoglycan is based upon LL-diaminopimelic acid (LL-DAP) without acetyl residues. The DNA base composition (mol % G+C) wss 67.6 (Table 2).

(iii) Physiological characteristics:

Physiological characteristics of the strain are summarized in Table 3.

The growth temperature ranged from 28° to 37° C. Catalase was weakly positive and oxidase negative. The strain liquefacted gelatin and produced caseinase and DNase but did not hydrolyse aesculine. Acid was produced from D-mannitol only but not from adonitol, L-arabinose, D-cellobiose, D-fructose, D-galactose, glucose, inositol, D-lactose, maltose, D-mannose, D-raffinose, L-rhamnose, D-ribose, D-sorbitol, sucrose, starch or D-xylose. Sodium acetate was utilized for the strain but sodium citrate not. Nitrate was reduced to nitrite.

(iv) Identification:

According to Bergey's Manual of Systematic bacteriology (Volume 2) and the above-mentioned characteristics, strain No. 1254 was considered to belong to the genus Pimelobacter.

Suzuki and Komagata (J. Gen. Microbiol. 29, 59-71, 1983) have proposed the new genus Pimelobacter to accommodate the LL-DAP-containing coryneform bacteria which was validated by IJSB (33, 672, 1983). Using DNA-DNA base-pairing methods they considered that new three species could be distinguished among LL-DAP-containing coryneform bacteria previously named *Arthrobacter simplex*, *A. tumescens* and *Brevibacterium lipolyticum*. The first, *Pimelobacter simplex*, contained most A. simplex strains and all *B. llipolyticum* strains, the second, *P. tumescens* contained *A. tumescens* strains while a third species, *P. jensenii*, was created for a single strain, NCIB9770, which was originally identified as *A. simplex* by Jensen and Gundersen. These three species of *P. simplex*, *P. tumescens* and *P. jensenii* were validated in genus Pimelobacter.

The physiological characteristics of strain No. 1254 were compared with those described by Suzuki and Komagata (1983) and differed from those of authentic three species. Therefore, strain No. 1254 was identified as Pimelobacter sp.

TABLE 1

| Morphological characteristics of strain No. 1254 | |
|---|---|
| Gram stain | positive |
| Cell shape | irregular rod occurs coccoid form in stationary phase culture |
| Spore | negative |
| Color of colony | cream white |

TABLE 2

| Phylogenetical characteristics of strain No. 1254 | |
|---|---|
| Cell wall peptidoglycan: | |
| Dianimo acid | LL-DAP |
| N-Glycolyl residue | negative (acetyl type) |
| Mol % G + C (HPLC) | 67.6 |

TABLE 3

| Physiological characteristics of strain No. 1254 | |
|---|---|
| Growth in aerobic condition | positive |
| Growth anaerobic condition | negative |
| Growth pH 6.8 (Nutrient broth) | positive |
| Growth pH 5.7 (Nutrient broth) | positive |
| Growth 2% NaCl (Nutrient broth) | negative |
| Growth 5% NaCl (Nutrient broth) | negative |
| Growth 7% NaCl (Nutrient broth) | negative |
| Growth 10% NaCl (Nutrient broth) | negative |
| Growth 0.01 mg/ml lysozyme (Mueller Hinton broth) | negative |
| Growth at 5° C. (Trypticase soy agar) | negative |
| Growth 18 (Trypticase soy agar) | positive |
| Growth 30 (Trypticase soy agar) | positive |
| Growth 37 (Trypticase soy agar) | positive |
| Growth 40 (Trypticase soy agar) | negative |
| Growth 55 (Trypticase soy agar) | negative |
| Motility | negative |
| Catalase | positive |
| Oxidase | negative |
| $H_2S$ (SIM medium) | negative |
| Indole | negative |
| Sodium citrate (Simmons) | negative |
| Sodium acetate | positive |
| Urease (Christensen) | positive |
| Gelatin liquefaction | positive |
| DNase | positive |
| Caseinase | positive |
| Gluconate oxidation | negative |
| Aesculine hydrolysis | negative |
| Nitrate reduction | positive |
| Acid production from adonitol | negative |
| Acid production from L-arabinose | negative |
| Acid production from D-cellobiose | negative |
| Acid production from D-fructose | negative |
| Acid production from D-galactose | negative |
| Acid production from glucose | negative |
| Acid production from inositol | negative |
| Acid production from D-lactose | negative |
| Acid production from maltose | negative |
| Acid production from D-mannitol | positive |
| Acid production from D-mannose | negative |
| Acid production from D-raffinose | negative |
| Acid production from L-rhamnose | negative |
| Acid production from D-ribose | negative |
| Acid production from D-sorbitol | negative |
| Acid production from starch | negative |
| Acid production from sucrose | negative |

TABLE 3-continued

Physiological characteristics of strain No. 1254

| | |
|---|---|
| Acid production from D-xylose | negative |

Taxonomic studies on *Bacillus megaterium* No. 1253 are as follows.

The methods described in Bergey's Manual of Systematic Bacteriology [Volume 2] were employed principally for this taxonomic study.

(i) Morphological characteristics:

Morphological observation of the strain No. 1253 was carried out with an optical microscope with cells cultured on nutrient broth (Difco) and trypticase soy agar (BBL) at 37° C. for 24 hours.

Strain No. 1253 was gram-positive straight rod and spore in endospores was mostly central position and sometimes in a terminal position without swelling of the sporangium and grown up to colonies with cream white on trypticase soy agar plate in air at 18° to 40° C.

(ii) Physiological characteristics

Physiological characteristics of the strain are summarized in Table 4.

Catalase, oxidase, urease and caseinase were positive.

Sodium citrate (Simmons) was utilized, aesculine hydrolysed, gelatin liquefacted, but nitrate was not reduced to nitrite. Acid was produced from L-arabinose, D-fructose, D-galactose, glucose, maltose, D-mannitol, starch and D-xylose, but not from D-lactose, D-mannose, L-rhamnose or D-sorbitol.

(iii) Identification:

According to Bergey's Manual of Systematic Bacteriology (Volume 2) and the above-mentioned physiological characteristics, strain No. 1253 was considered to belong to the genus Bacillus, and nearly to *B. megaterium* or *B. circulans*.

N. A. Logan and R. C. W. Berkeley et al. showed detailed data on physiological characteristics of *B. megaterium* and *B. circulans* (J. Gen. Microbiol. 130, 1871–1880, 1984).

According to their data, the strain was different from *B. circulans* in characteristics of swelling of the sporangium, growth in 0.01 mg/ml lysozyme, citrate utilization and acid production from D-mannose and rhamnose. Therefore, strain No. 1253 was identified as *B. megaterium*.

(continued on the next page)

TABLE 4

Physiological characteristics of strain No. 1253

| | |
|---|---|
| Shape | G(+)Rod |
| Spore | positive |
| Growth in aerobic condition | positive |
| Growth pH 6.8 (Nutrient broth) | positive |
| Growth pH 5.7 (Nutrient broth) | positive |
| Growth 2% NaCl (Nutrient broth) | positive |
| Growth 5% NaCl (Nutrient broth) | negative |
| Growth 7% NaCl (Nutrient broth) | negative |
| Growth 10% NaCl (Nutrient broth) | negative |
| Growth 0.01 mg/ml lysozyme (Mueller Hinton broth) | negative |
| Growth at 5° C. (Trypticase soy agar) | negative |
| Growth 18 (Trypticase soy agar) | positive |
| Growth 30 (Trypticase soy agar) | positive |
| Growth 37 (Trypticase soy agar) | positive |
| Growth 40 (Trypticase soy agar) | positive |
| Growth 55 (Trypticase soy agar) | negative |
| Motility | negative |
| Catalase | positive |
| Oxidase | positive |
| H$_2$S (SIM medium) | negative |
| Indole | negative |

TABLE 4-continued

Physiological characteristics of strain No. 1253

| | |
|---|---|
| Sodium citrate (Simmons) | positive |
| Urease (Christensen) | positive |
| Gelatin liquefaction | positive |
| Caseinase | positive |
| Aesculine hydrolysis | positive |
| Nitrate reduction | negative |
| Acid production from L-arabinose | positive |
| Acid production from D-fructose | positive |
| Acid production from D-galactose | positive |
| Acid production from glucose | positive |
| Acid production from D-lactose | negative |
| Acid production from maltose | positive |
| Acid production from D-mannitol | positive |
| Acid production from D-mannose | negative |
| Acid production from L-rhamnose | negative |
| Acid production from D-sorbitol | negative |
| Acid production from starch | positive |
| Acid production from D-xylose | positive |
| Mol % G + C (HPLC) | 39.0 |

(3) METHOD 3

The compound (V) can be prepared by introducing a hydroxy-protective group into the compound (IV).

The introducing agent of the hydroxy-protective group used in this reaction may include trisubstituted silyl halide such as tri(lower)alkylsilyl halide (e.g. trimethylsilyl chloride, t-butyldimethylsilyl chloride, etc.), an acylating agent such as those given in the explanation of Method 1.

This reaction is preferably carried out in the presence of a base such as those exemplified in Method 1.

Further, this reaction is usually carried out in a conventional solvent which does not adversely influence the reaction such as N,N-dimethylformamide, and the like.

The reaction temperature is not critical and the reaction is usually carried out under cooling to warming.

(4) METHOD 4

The compound (VII) or its salt can be prepared by subjecting the compound (V) to a stereoselective addition of the compound (VI) or its salt.

Suitable salt of the compounds (VI) and (VII) may include conventional acid addition salt such as hydrochloride, hydrobromide, sulfate, formate, acetate, and the like.

This reaction is usually carried out in a conventional solvent which does not adversely influence the reaction such as a protic solvent (e.g. methanol ethanol, etc.), and the like.

The reaction temperature is not critical and the reaction is usually carried out under cooling to warming.

(5) METHOD 5

The compound (VIII) can be prepared by subjecting the compound (VII) or its salt to cyclization reaction.

The reagent used in this cyclization may include one which is capable of cyclizing a β-amino carboxylate to a β-lactam such as Grignard reagent, for example, arylmagnesium halide (e.g. phenylmagnesium iodide, mesitylmagnesium bromide, etc.), lower alkylmagnesium halide (e.g. methylmagnesium bromide, ethylmagnesium bromide, t-butylmagnesium chloride, etc.), and the like.

This reaction is usually carried out in a conventional solvent which does not adversely influence the reaction such as tetrahydrofuran, and the like.

The reaction temperature is not critical and the reaction is usually carried out under cooling to warming.

Among the object compound (VIII), the compound (VIIIa) as formulated above is new and is the most important compound for preparing the compound (I).

(6) METHOD 6

The compound (I) can be prepared by removing the amino-protective group of the compound (VIII).

This removal reaction can be carried out in a conventional manner which is applicable to transform a protected amino group to an amino group such as hydrolysis, reduction, oxidative debenzylation, and the like.

In case that the amino-protective group is "mono or diarylmethyl, in which the aryl moiety is substituted with at least one lower alkoxy group", the removal reaction is preferably carried out by a so-called "oxidative debenzylation" using potassium persulfate in the presence of water and this reaction is preferably carried out around neutral condition, and for this purpose, a neutralizing agent such as dipotassium hydrogenphosphate is usually added to the reaction mixture.

(7) METHOD 7

The compound (X) or its salt can be prepared by subjecting the compound (IX) to removal reaction of the amino protective group of $R_b{}^3$.

Suitable salts of the compound (X) may be the same as those for the compound (VI).

The present reaction is usually carried out by a conventional method such as hydrolysis, reduction, and the like.

(i) Hydrolysis :

Hydrolysis is preferably carried out in the presence of a base or an acid. Suitable base may include an alkali metal hydroxide (e.g. sodium hydroxide, potassium hydroxide,.etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using tirfluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction :

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(8) METHOD 8

The compound (XI) or its salt can be prepared by introducing a silyl group into the compound (X) or its salt.

Suitable introducing agent of the silyl group used in this reaction may include a conventional one which is capable of introducing the silyl group as mentioned above into the compound (X), for example, trisubstituted silyl halide such as tri(lower)alkylsilyl halide (e.g. trimethylsilyl chloride, t-butyldimethylsilyl chloride, etc.), bis(trisubstituted silyl)amine such as bis[tri(lower)alkylsilyl]amine (e.g. 1,1,1,3,3,3-hexamethyldisilazane, 1,1,1,3,3,3-hexaethyldisilazane, etc.], and the like.

This reaction is preferably carried out in the presence of a base such as those exemplified in Method 1.

The reaction can be carried out in a conventional solvent which does not adversely influence the reaction such as acetone, dioxane, acetonitrile, chloroform, benzene, dichloromethane, dichloroethane, tetrahydrofuran, ethyl acetate, N,N-dimethylformamide, pyridine, hexamethylphosphoramide, etc., or a mixture thereof.

The reaction temperature is not critical and the reaction is usually carried out under cooling to heating.

The compounds (I), (III), (IV), (V), (VII), (VIII), (X) and (XI) obtained in the above-mentioned Methods 1 to 8 can be isolated and purified in a conventional manner such as distillation, crystallization, chromatography, and the like.

The optically active 3-substituted azetidinones (I) prepared stereoselectively and in high yield in accordance with the new process of the present invention can be transformed into the principal intermediate (A) by known methods, which is used for manufacturing β-lactam antibiotics such as penems, carbapenems, cephalosporins, and the like, and therefore the process of the present invention is very important and quite valuable for industrial production of the said intermediate (A).

Further, the optically active 1,3-disubstituted azetidinones (VIIIa) are a useful intermediate for production of the principal intermediate (A).

The following examples are given for the purpose of only illustrating the present invention.

EXAMPLE 1

To a solution of ethyl 2-(1-hydroxyethyl)acrylate (40 g) and pyridine (26.9 ml) in dichloromethane (277 ml) was added dropwise acetyl chloride (23.7 ml) at 0° C. The reaction mixture was stirred for 1 hour and quenched with water (200 ml). The aqueous layer was separated and extracted twice with dichloromethane. The combined organic layers were washed with 1N hydrochloric acid, saturated aqueous sodium hydrogen carbonate water and an aqueous sodium chloride in turn, and then, dried over magnesium sulfate. After the resultant solution was evaporated, the residue was distilled in vacuo to give ethyl 2-(1-acetoxyethyl)acrylate (41.44 g) as a colorless oil.

bp : 58° C./5 mmHg
IR (Neat) : 1740, 1720 cm$^{-1}$
NMR (CDCl$_3$, δ) : 1.309 (3H, t, J=7.13Hz), 1.404 (3H, d, J=6.51Hz), 2.074 (3H, s), 4.236 (2H, q, J=7.12Hz), 5.713 (1H, q, J=6.68Hz), 5.805 (1H, t, J=1.08Hz), 6.282 (1H, s)

EXAMPLE 2

To a solution of methyl 2-(1-hydroxyethyl)acrylate (50 g) and pyridine (32.6 ml) in dichloromethane (200 ml) was added dropwise acetyl chloride (34.8 g) at 0° C. After the reaction mixture was stirred for 1 hour, the mixture was allowed to warm to room temperature, and quenched with water (500 ml). The aqueous layer was separated and extracted twice with dichloromethane. The combined organic layer were washed with 1N hydrochloric acid, saturated aqueous sodium hydrogencarbonate and an aqueous sodium chloride in turn, and then dried over magnesium sulfate. The resultant solution was evaporated, and the residue was distilled in vacuo to give methyl 2-(1-acetoxyethyl)acrylate (28.2 g).

bp : 53° C./2 mmHg
IR (Neat) : 1735 cm$^{-1}$
NMR (CDCl$_3$, δ) : 1.403 (3H, d, J=6.48Hz), 2.076 (3H, s), 3.782 (3H, s), 5.706 (1H, qd, J=6.49 and 1.12Hz), 5.825 (1H, d, J=1.12Hz), 6.285 (1H, s)

EXAMPLE 3

A mixture of methyl 2-(1-acetoxyethyl)acrylate (5 g) and "Lipase P" (Trademark; origin : Pseudomonas sp.; maker : Amano Pharmaceutical Co.) (1.25 g) in phosphate buffer solution (0.1M) pH 7.0 (400 ml) was stirred at room temperature for 55 hours. The whole mixture was extracted with ethyl acetate three times and the combined extracts were dried. After removal at the solvent in vacuo, the crude product was purified by column chromatography on silica gel (eluent : a mixture of hexane and ethyl acetate, 2:1). The resultant oily residue (840 mg) was distilled in vacuo to give methyl 2-[(1R)-1-hydroxyethyl]acrylate (644 mg).

bp : 60°-80° C./5 mmHg (bulb to bulb)
[α]$_D^{30}$: +17.64° (C=1.27, CHCl$_3$)
IR (Neat) : 3400, 1710 cm$^{-1}$

EXAMPLE 4

A mixture of ethyl 2-(1-acetoxyethyl)acrylate (1 g) and Lipase (0.25 g) in 0.1M phosphate buffer solution (pH 7.0) (80 ml) was stirred at room temperature for 60 hours. The whole mixture was extracted three times with ethyl acetate and the combined extracts were dried over magnesium sulfate. After removal of the solvent in vacuo, the crude product was purified by column chromatography on silica gel (eluent : a mixture of hexane and ethyl acetate, 2:1) to give ethyl 2-[(1R)-1-hydroxyethyl]acrylate (298 mg).

IR (Neat) : 3420, 1710 cm$^{-1}$
NMR (CDCl$_3$, δ) 1.36 (3H, t, J=6.0Hz), 1.50 (3H, d, J=7.0Hz), 3.42 (1H, br. s), 4.29 (2H, q, J=6.0Hz), 4.85 (1H, m), 5.90 (1H, s), 6.29 (1H, s)

EXAMPLE 5

To a suspension of ethyl 2-(1-hydroxyethyl)acrylate (40 g) and imidazole (28.3 g) in N,N-dimethylformamide (200 ml) was added portionwise t-butyldimethylsilyl chloride (46 g) at 0° C. After the mixture was stirred for 10 hours, the reaction mixture was poured into a mixture of water and ethyl acetate. The aqueous layer was separated and extracted twice with ethyl acetate. The combined organic layers were washed with water, 1N hydrochloric acid, saturated aqueous sodium hydrogencarbonate, water and an aqueous sodium chloride in turn, and then dried over magnesium sulfate. The evaporation of the solution gave ethyl 2-[1-(t-butyl-dimethylsilyloxy)ethyl]acrylate (68.5 g).

IR (Neat) : 1720 cm$^{-1}$
NMR (CDCl$_3$, δ) : 0.036 (3H, s), 0.072 (3H, s), (3H, t, J=7.12Hz), 4.143 (2H, dq, J=7.12, 1.46Hz), 4.691 (1H, ddq, J=6.24, 1.74, 1.18Hz), 5.937 (1H, dd, J=1.74, 1.74Hz), 6.185 (1H, dd, J=1.74 and 1.18Hz)

EXAMPLE 6

To a solution of ethyl 2-[1-(t-butyldimethylsilyloxy)ethyl]acrylate (5 g) in methanol (50 ml) was added 4-methoxybenzylamine (2.65 g) at room temperature. After stirring for 2 days, the solvent was removed from the reaction mixture. The residue was columnchromatographed on silica gel in a usual manner (eluent : a mixture of hexane and ethyl acetate, 2:1 to 1:1) to give ethyl (2S*,3R*)-3-(t-butyldimethylsilyloxy)-2-(4-methoxybenzylaminomethyl)butanoate (6.435 g).

IR (Neat) : 3350, 1730 cm$^{-1}$
NMR (CDCl$_3$, δ) : 0.025 (6H, s), 0.806 (9H, s), 1.122 (3H, d, J=6.15Hz), 1.220 (3H, t, J=7.13Hz), 1.636 (1H, br. s), 2.513-2.616 (1H, m), 2.770-2.948 (2H, m), 3.677 (2H, s), 3.752 (3H, s), 3.967-4.164 (1H, m), 4.110 (2H, q, J=7.13Hz), 6.769-6.840 (2H, m), 7.145-7.202 (2H, m)
MASS : M$^+$=395

EXAMPLE 7

To a solution of ethyl (2S*,3R*)-3-(t-butyldimethylsilyloxy)-2-(4-methoxybenzylaminomethyl)butanoate (6 g) in tetrahydrofuran (303 ml) was added dropwise a solution of mesitylmagnesium bromide (1M, 24.3 ml) in tetrahydrofuran at room temperature. After stirring for 30 minutes, water (10 ml) was added dropwise to the reaction mixture and the solvent was removed under reduced pressure. To the residue were added ethyl acetate and water, then the aqueous layer was separated and extracted twice with ethyl acetate. The combined organic layers were washed with 1N hydrochloric acid, saturated aqueous sodium hydrogencarbonate, water and an aqueous sodium chloride in turn and then dried over magnesium sulfate. The resultant solution was evaporated under reduced pressure and the residue was column-chromatographed on silica gel (eluent : a mixture of hexane and ethyl acetate, 3:1) to give (3S*)-3-[(1R*)-1-(t-butyldimethylsilyloxy)ethyl]-1-(4-methoxybenzyl)azetidin-2-one (4.8 g), which contained about 2% of the corresponding (3R*), (1R*)-isomer.

IR (Neat) : 1750, 1610 cm$^{-1}$

NMR (CDCl$_3$, δ) : 0.055 (3H, s), 0.066 (3H, s), 0.854 (6H, s), 1.170 (3H, d, J=6.22Hz), 3.065-3.187 (2H, m), 3.803 (3H, s), 4.141-4.222 (1H, m), 4.213 (1H, d, J=15.0Hz), 4.383 (1H, d, J=15.0Hz), 6.829-6.901 (2H, m), 7.152-7.195 (2H, m)

The same product could be obtained using the following Grignard Reagent instead of mesitylmagnesium bromide.

| Grignard Reagent | Amount | Reaction Temperature | Yield |
| --- | --- | --- | --- |
| ethylmagnesium bromide | 1.6 eq. | room temp. | 42% |
| t-butylmagnesium chloride | 3.0 eq. | room temp. | 90% |
| phenylmagnesium iodide | 1.6 eq. | room temp. | 62% |
| Example 8 | | | |

EXAMPLE 8

To a solution of ethyl (2-[1-(t-butyldimethyl-silyloxy)ethyl]acrylate (5 g) in methanol (100 ml) was added 4-methoxybenzylamine (2.65 g) at room temperature. After two days, the solvent was evaporated and the residual methanol was azeotropically removed using toluene. To the residual product was added tetrahydrofuran (387 ml) and the solution was stirred at room temperature. To this solution was added dropwise mesitylmagnesium bromide in tetrahydrofuran (1M, 31 ml) at room temperature. After stirring for 30 minutes, the reaction mixture was quenched with water and evaporated. The aqueous layer was extracted twice with ethyl acetate. The combined organic layers were washed with 1N hydrochloric acid, saturated aqueous sodium hydrogencarbonate, water and an aqueous sodium chloride in turn, and then dried over magnesium sulfate. The resultant solution was evaporated and the residue was column-chromatographed on silica gel (eluent : a mixture of hexane and ethyl acetate, 3:1) to give (3S*)-3-[(1R*)-1-(t-butyldimethylsilyloxy)ethyl]-1-(4-methoxybenzyl)azetidin-2-one (4.5 g).

IR (Neat) : 1750, 1610 cm$^{-1}$

EXAMPLE 9

A mixture of (3S*)-3-[(1R*)-1-(t-butyldimethylsilyloxy)ethyl]-1-(4-methoxybenzyl)azetidin-2-one (1.74 g), potassium persulfate (2.7 g) and dipotassium hydrogen phosphate (3.48 g) in acetonitrile (30 ml) and water (20 ml) was stirred at 70° C. for 5 hours. The mixture was evaporated and the residual aqueous layer was extracted with ethyl acetate. The extract was washed with 1N hydrochloric acid, saturated aqueous sodium hydrogencarbonate, water and an aqueous sodium chloride in turn, and then dried over magnesium sulfate. The resultant solution was evaporated, and the residue was column-chromatographed on silica gel (eluent : a mixture of hexane and ethyl acetate, 1:1) to give (3S*)-3-[(1R*)-(1-t-butyldimethylsilyloxy)ethyl]acetidin-2-one (722 mg).

IR (CHCl$_3$, δ) : 3420, 1752 cm$^{-1}$
NMR (CDCl$_3$, TMS) : 0.078 (6H, s), 0.875 (9H, s), 1.199 (3H, d, J=6.34Hz), 3.162-3.372 (3H, m), 4.214 (1H, dq, J=4.35, 6.20Hz), 5.774 (1H, br s)

EXAMPLE 10

A mixture of ethyl 2-(1-acetoxyethyl)acrylate (35.65 g) and "Lipase P" (8.88 g) in pH 7.0 phosphate buffer (0.1M) (2.8 l) was stirred at 37° C. for 72 hours. The whole mixture was extracted with ethyl acetate, and the combined extracts were dried. After removal at the solvent from the solution in vacuo, the crude product was purified by column-chromatography on silica gel (eluent : a mixture of hexane and ethyl acetate, 2:1) to give ethyl 2-[(1R)-1-hydroxyethyl]acrylate (11.40 g).

bp : 54°-57° C./5 mmHg
[α]$_D^{31}$ : +17.62° (C=1.042, CHCl$_3$)
IR (Neat) : 3420, 1710, 1630 cm$^{-1}$
NMR (CDCl$_3$, δ) : 1.326 (3H, t, J=7.12Hz), 1.393 (3H, d, J=6.46Hz), 2.730 (1H, br s), 4.251 (2H, q, J=7.12Hz), 4.620 (1H, q, J=6.46Hz), 5.807 (1H, s), 6.216 (1H, s)

EXAMPLE 11

To a suspension of ethyl 2-[(1R)-1-hydroxyethyl]acetylate (11.22 g) and imidazole (6.89 g) in N,N-dimethylformamide (110 ml) was added portionwise t-butyldimethylsilyl chloride (14.08 g) at 0° C. After the mixture was stirred for 10 hours, the reaction mixture was poured into a mixture of water and ethyl acetate. The water layer was separated and extracted twice with ethyl acetate. The combined organic layers were washed with water, 1N hydrochloric acid, saturated aqueous sodium hydrogencarbonate, water and an aqueous sodium chloride, and then, dried over magnesium sulfate. The resultant solution was evaporated, and the residue was distilled to give ethyl 2-[(1R)-1-(t-butyldimethylsilyloxy)ethyl]-acrylate (19.53 g).

bp : 74°-75° C./3 mmHg
[α]$_D^{30}$ : +29.5° (C=1.01, CHCl$_3$)
IR (Neat) : 1715, 1630 cm$^{-1}$
NMR (CDCl$_3$, δ) : 0.036 (3H, s), 0.071 (3H, s), 0.902 (9H, s), 1.277 (3H, d, J=6.21Hz), 1.308 (3H, t, J=7.13Hz), 4.214 (2H, dq, J=7.13Hz, 1.40Hz), 4.690 (1H, q, J=6.21Hz), 5.936 (1H, t, J=1.72Hz), 6.184 (1H, t, J=1.40Hz)

EXAMPLE 12

To a solution of ethyl 2-[(1R)-1-(t-butyldimethylsilyloxy)ethyl]acrylate (15 g) in methanol (300 ml) was added 4-methoxybenzylamine (8.05 g) at room temperature. After stirring for 2 days, the solvent was removed by evaporation to give crude ethyl (2S,3R)-3-(t-butyldimethylsilyloxy)-2-(4-methoxybenzylaminomethyl)-butanoate (25.14 g).

This product was used as the starting compound of the subsequent reaction without further purification.

IR (CHCl$_3$) 1730, 1610, 1585 cm$^{-1}$

EXAMPLE 13

To a solution of ethyl (2S,3R)-3-(t-butyldimethylsilyloxy)-2-(4-methoxybenzylaminomethyl)butanoate (7.91 g, crude) in tetrahydrofuran (200 ml) was added dropwise mesitylmagnesium bromide (29 ml) at room temperature. After stirring for 30 minutes, the mixture was quenched with 0.2N hydrochloric acid (250 ml) ethyl acetate (200 ml). The aqueous layer was separated and extracted twice with ethyl acetate. The combined organic layers were washed with 1N hydrochloric acid, saturated aqueous sodium hydrogencarbonate, water and an aqueous sodium chloride in turn, and then dried over magnesium sulfate. The resultant solution was evaporated, and the residue was purified by column-chromatography to give (3S)-3-[(1R)-1-(t-butyldimethylsilyloxy)ethyl]-1-(4-methoxybenzyl)azetidin-2-one (3.55 g).

[α]$_D^{30}$ : −27.21° C. (C=1.176, CHCl$_3$)
IR (CHCl$_3$) 1735, 1610, 1585 cm$^{-1}$

NMR (CDCl$_3$, δ) : 0.054 (3H, s), 0.065 (3H, s), 0.853 (9H, s), 1.169 (3H, d, J=6.22Hz), 3.048–3.187 (3H, m), 3.802 (3H, s), 4.130–4.222 (1H, m), 4.213 (1H, d, Jab=14.95Hz), 4.335 (1H, d, Jab=14.95Hz), 6.865 (2H, d, J=867Hz), 7.174 (2H, d, J=8.67Hz)

The above product contained a very small amount (less than 3%) of the corresponding (3R)-isomer.

EXAMPLE 14

A mixture of (3S)-3-[(1R)-1-(t-butyldimethylsilyloxy)ethyl]-1-(4-methoxybenzyl)azetidin-2-one (2.45 g), potassium persulfate (4.73 g) and dipotassium hydrogen phosphate (3.66 g) in acetonitrile (35 ml) and water (30 ml) was stirred at 70° C. for 2 hours. The mixture was evaporated and the residue was extracted with ethyl acetate. The extract was washed with 1N hydrochloric acid, saturated aqueous sodium hydrogencarbonate, water and an aqueous sodium chloride in turn, and then dried over magnesium sulfate. The resultant solution was evaporated and the residue was column-chromatographed on silica gel (eluent : a mixture of hexane and ethyl acetate, 3:1) to give (3S)-3-[(1R)-1-(t-butyldimethylsilyloxy)ethyl]azetidin-2-one (0.71 g).

mp : 64°–66° C.
$[\alpha]_D^{28}$ : −57.64° (C=1.112, CHCl$_3$)
IR (CHCl$_3$) 3410, 1755 cm$^{-1}$
NMR (CDCl$_3$, δ) : 0.078 (6H, s), 0.876 (9H, s), 1.200 (3H, d, J=6.26Hz), 3.190–3.373 (3H, m), 4.215 (1H, m), 5.753 (1H, br. s)

The product was recrystallized from hexane to give a purified product (237 mg).
$[\alpha]_D^{28}$ : −66.34° (C=1.01, CHCl$_3$)

EXAMPLE 15

To a solution of ethyl 2-[(1R)-1-(t-butyldimethylsilyloxy)ethyl]acrylate (25.84 g) in methanol (517 ml) was added benzylamine (11.79 g) at room temperature. After stirring for 6 days, 10% palladium hydroxide on carbon (2.58 g) was added and the mixture was stirred under hydrogen atmosphere for 5 hours. After the termination of reaction, the mixture was concentrated to give crude ethyl (2S,3R)-2-aminomethyl-3-(t-butyldimethylsilyloxy)butanoate (28.02 g). This compound was immediately used as the starting compound for the next transformation without further purification.

IR (neat) : 3370, 1725 cm$^{-1}$
NMR (CDCl$_3$, δ) : 0.048 (3H, s), 0.059 (3H, s), 0.871 (9H, s), 1.181 (3H, d, J=6.19Hz), 1.27921 (3H, t, J=7.13Hz), 1.488 (2H, br s), 2.428 (1H, ddd, J=4.88, 7.81 and 6.99Hz), 2.995 (1H, d, J=4.88Hz), 3.008 (1H, d, J=7.81Hz), 4.114 (1H, dt, J=6.99Hz and 6.19Hz), 4.168 (2H, q, J=7.13Hz)

EXAMPLE 16

A mixture of ethyl (2S,3R)-2-aminomethyl-3-(t-butyldimethylsilyloxy)butanoate (1.38 g) and 1,1,1,3,3,3-hexamethyldisilazane (1.58 ml) was stirred at 70° C. for 15 hours, and then concentrated under reduced pressure. The residue was dissolved in 50 ml of tetrahydrofuran and 1.1N t-butylmagnesium chloride in tetrahydrofuran (15 ml) was added dropwise thereto at room temperature. After stirring for 30 minutes, the reaction mixture was quenched with water (10 ml), and diluted with ethyl acetate (50 ml) and 1N hydrochloric acid in water (20 ml). The aqueous layer was separated and extracted twice with ethyl acetate (25 ml×2) and the combined organic layers were washed in turn with 1N hydrochloric acid in water (20 ml), saturated sodium bicarbonate (20 ml), water (20 ml) and brine (20 ml), dried over magnesium sulfate and evaporated under reduced pressure. The residue was column-chromatographed on silica gel (hexane-ethyl acetate=3:1) to give (3S)-3-[(1R)-1-(t-butyldimethylsilyloxy)ethyl]-azetidin-2-one (0.841 g).

$[\alpha]_D^{25}$ : −67.7° (C=1.12, CHCl$_3$)
IR (CHCl$_3$) 3410, 1750 cm$^{-1}$
NMR (CDCl$_3$, δ) : 0.078 (6H, s), 0.876 (9H, s), 1.200 (3H, d, J=6.26Hz), 3.19–3.373 (3H, m), 4.215 (1H, m), 5.753 (1H, br s)

EXAMPLE 17

To a solution of ethyl (2S,3R)-2-aminomethyl-3-(t-butyldimethylsilyloxy)butanoate (1.38 g) and triethylamine (0.84 ml) in tetrahydrofuran (10 ml) was added dropwise chlorotrimethylsilane (0.76 ml) at room temperature. After stirring for 1 day, the precipitate was filtered and the filtrate was evaporated under reduced pressure. The residue was dissolved in tetrahydrofuran (50 ml) and 1.1N t-butylmagnesium chloride in tetrahydrofuran (15 ml) was added dropwise thereto at room temperature. After stirring for 30 minutes, the reaction mixture was quenched with water (10 ml), and diluted with ethyl acetate (50 ml) and 1N hydrochloric acid in water (20 ml). The aqueous layer was separated and extracted twice with ethyl acetate (25 ml×2) and the combined organic layer was washed in turn with 1N hydrochloric acid in water (20 ml), saturated aqueous sodium bicarbonate (20 ml), water (20 ml) and brine (20 ml), dried over magnesium sulfate and evaporated under reduced pressure. The residue was column-chromatographed on silica gel (hexane-ethyl acetate=3:1) to give (3S)-3-[(1R)-1-(t-butyldimethylsilyloxy)ethyl]-azetidin-2-one (0.543 g).

$[\alpha]_D^{25}$ −67.4° (C=1.07, CHCl$_3$)
IR (CHCl$_3$) 3410, 1750 cm$^{-1}$
NMR (CDCl$_3$, δ) : 0 078 (6H, s), 0.876 (9H, s), 1.200 (3H, d, J=6.26Hz), 3.190–3.373 (3H, m), 4.215 (1H, m), 5.753 (1H, br s)

EXAMPLE 18

A loopful of slant culture of Pimelobacter sp. No. 1254 was inoculated to a medium (80 ml) containing bouillon 1%, glucose 1% and calcium carbonate 0.2%. The flash was incubated with shaking for 24 hours at 30° C. The resultant seed culture (1.6 ml) was inoculated to the same medium (80 ml) and cultured for 2 days at 30° C. Thirty (30) ml of this cultured broth, 3 ml of 1M phosphate buffer (pH 7.5) and 1 g of ethyl 2-(1-acetoxyethyl)acrylate were poured into a 250 ml widemouth flask and incubated for 20 hours at 30° C. with shaking. The whole mixture was extracted twice with 40 ml of ethyl acetate and the combined extract was dried. After removal of the solvent in vacuo, the crude material was applied on a silica gel column and developed with a mixture of n-hexane and ethyl acetate (4:1). The fractions containing the desired compounds were collected and dried in vacuo to give 227 mg of ethyl 2-[(1R)-1-hydroxyethyl]acrylate.

IR (Neat) : 3420, 1710 cm$^{-1}$

EXAMPLE 19

A loopful of slant culture of *Bacillus megaterium* No. 1253 was inoculated to a medium (80 ml) containing bouillon 1%, glucose 1% and calcium carbonate 0.2%. The flash was incubated with shaking for 24 hours at 30° C. The resultant seed culture (1.6 ml) was inoculated to the same medium (80 ml) and cultured for 2 days at 30° C. Eighty (80) ml of this cultured broth, 3 ml of 1M phosphate buffer (pH 7.5) and 1 g of ethyl 2-(1-acetoxyethyl)acrylate were poured into a 250 ml widemouth flask and incubated for 20 hours at 30° C. with shaking. The whole mixture was extracted twice with 40 ml of ethyl acetate and the combined extract was dried. After removal of the solvent in vacuo, the crude material was applied on a silica gel column and developed with a mixture of n-hexane and ethyl acetate (4:1). The fractions containing the desired compounds were collected and dried in vacuo to give 250 mg of ethyl 2-[(1R)-1-hydroxyethyl]acrylate.

IR (Neat) : 3420, 1710 cm$^{-1}$

What we claim is:

1. A process for preparing optically active 3-substituted azetidinones of the formula:

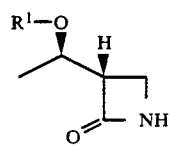
(I)

in which $R^1$ is a hydroxy-protective group, which comprises (1) acylating a compound of the formula:

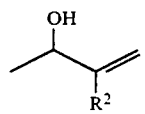
(II)

in which
$R^2$ is a protected carboxy, to give a compound of the formula:

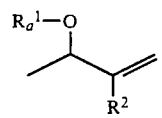
(III)

in which
$R_a^1$ is acyl and
$R^2$ is as defined above, and (2) subjecting the compound (III) to enzymatic hydrolysis to give a compound of the formula:

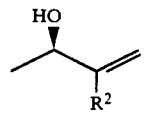
(IV)

in which $R^2$ is as defined above, wherein the enzyme to be used is derived from the microorganism belonging to genus Pimelobacter or is *Bacillus megaterium No.* 1253, (3) introducing a hydroxy-protective group into the compound (IV) to give a compound of the formula:

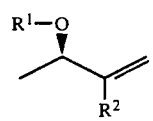
(V)

in which
$R^1$ is hydroxy-protective group and
$R^2$ is as defined above, and (4) subjecting the compound (V) to a stereoselective addition reaction of a compound of the formula:

$R^3$—NH$_2$ (VI)

in which
$R^3$ is hydrogen or amino-protective group, or its salt to give a compound of the formula:

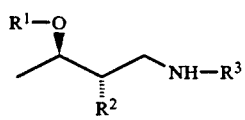
(VII)

in which $R^1$, $R^2$ and $R^3$ are each as defined above, or its salt, and (5) if necessary, subjecting a compound of the formula:

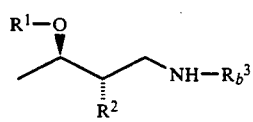
(IX)

in which
$R^1$ and $R^2$ are each as defined above, and
$R_b^3$ is an amino-protective group, to a removal reaction of the amino-protective group to give a compound of the formula:

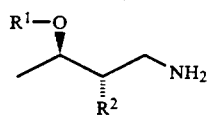
(X)

in which $R^1$ and $R^2$ are each as defined above, or its salt, and (6) if necessary, introducing a silyl group into the compound (X) or its salt to give a compound of the formula:

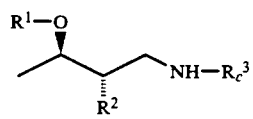
(XI)

in which
$R^1$ and $R^2$ are each as defined above, and
$R_c^3$ is a silyl group, or its salt, and (7) subjecting the compound (VII) to a cyclization reaction to give a compound of the formula:

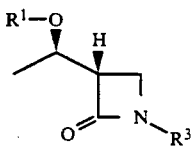
(VIII)

in which
$R^1$ and $R^3$ are each defined above, and (8) if necessary, removing the amino-protective group of a compound of the formula:

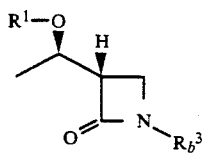 (XII)

in which
R$^1$ and R$_b^3$ are each as defined above, to give the compound (I).

2. The process of claim 1, wherein
R$^1$ is tri(lower)alkylsilyl or lower alkanoyl,
R$_a^1$ is lower alkanoyl,
R$^2$ is lower alkoxycarbonyl,
R$^3$ is hydrogen, mono(or di)arylmethyl, in which the aryl moiety is substituted with at least one lower alkoxy group, or tri(lower)alkylsilyl,
R$_b^3$ is mono(or di)arylmethyl, in which the aryl moiety is substituted with at least one lower alkoxy group, or tri(lower)alkylsilyl, and
R$_c^3$ is tri(lower)alkylsilyl.

3. A process for preparing optically active compound of the formula:

(IV)

in which R$^2$ is as defined above, which comprises subjecting a compound of the formula:

(III)

in which
R$_a^1$ is acyl and
R$^2$ is as defined above, to an enzymatic hydrolysis wherein the enzyme to be used is derived from the microorganism belonging to genus Pimelobacter or is *Bacillus megaterium* No. 1253.

4. The process of claim 1, 2, or 3, wherein the enzyme to be used is selected from the group consisting of Pimelobacter sp. No. 1254 and *Bacillus megaterium* No. 1253.

* * * * *